(12) United States Patent
Ponzone

(10) Patent No.: US 7,910,334 B2
(45) Date of Patent: Mar. 22, 2011

(54) BIOTRANSFORMATION OF COLCHICINOID COMPOUNDS

(75) Inventor: Cesare Ponzone, Milan (IT)

(73) Assignee: Indena S.p.A., Milan (IT)

( * ) Notice: Subject to any disclaimer, the term of this patent is extended or adjusted under 35 U.S.C. 154(b) by 776 days.

(21) Appl. No.: 11/596,091

(22) PCT Filed: May 12, 2004

(86) PCT No.: PCT/EP2004/005074
§ 371 (c)(1),
(2), (4) Date: Dec. 4, 2007

(87) PCT Pub. No.: WO2005/108595
PCT Pub. Date: Nov. 17, 2005

(65) Prior Publication Data
US 2009/0011479 A1    Jan. 8, 2009

(51) Int. Cl.
*C12P 19/44*    (2006.01)

(52) U.S. Cl. ....... 435/74; 435/127; 435/78; 435/252.31; 435/170

(58) Field of Classification Search ............. 435/74, 435/78, 127, 252.31, 170
See application file for complete search history.

(56) References Cited

U.S. PATENT DOCUMENTS

| | | | |
|---|---|---|---|
| 3,775,252 A * | 11/1973 | Kinsel et al. | 435/255.5 |
| 3,888,737 A * | 6/1975 | Watanabe et al. | 435/115 |
| 6,329,192 B1 * | 12/2001 | Ben-Bassat et al. | 435/252.1 |
| 6,372,458 B1 * | 4/2002 | Bombardelli et al. | 435/74 |
| 2001/0055796 A1 * | 12/2001 | Seo et al. | 435/158 |

FOREIGN PATENT DOCUMENTS

WO    98/15642 A    4/1998

OTHER PUBLICATIONS

Solet J-M et al: "Glucosylation of thiocolchichine by a cell suspension . . . asiatica", vol. 33, No. 4, Jul. 6, 1993, pp. 817-820.

* cited by examiner

*Primary Examiner* — Sandra Saucier
*Assistant Examiner* — Susan Hanley
(74) *Attorney, Agent, or Firm* — Ladas & Parry LLP

(57) ABSTRACT

The present invention relates to a biotransformation process, effected by means of selected microbial strains, for the preparation of 3-O-glycosyl derivatives of colchicinoid compounds.

9 Claims, No Drawings

BIOTRANSFORMATION OF COLCHICINOID COMPOUNDS

This application is a national stage entry of PCT/EP04/05074, filed May 12, 2004, the disclosure of which is incorporated by reference.

The present invention relates to a biotransformation process, effected by means of selected microbial strains, for the preparation of 3-O-glycosyl derivatives of colchicinoid compounds.

In particular, the process of the present invention provides colchicinoid compounds glycosylated exclusively at C-3 of the aromatic ring A, starting from colchicine, thiocolchicine or the derivatives thereof. The process, resulting in high productivity and purity of the obtained product, is based on an early activation of the glycosylating enzyme, determined by a demethylated colchicine intermediate. Preferably, the process of the invention consists of a multiple feed-batch fermentation process, comprising the fractionated feeding of a nitrogen source, a carbon source and the substrate to be transformed.

The colchicinoid compounds glycosylated at C-3 of the benzene ring are of remarkable pharmacological importance in view of their high effectiveness and as intermediates for the preparation of new medicaments.

In particular, thiocolchicoside (3-O-glucosylthiocolchicine) is an attractive and interesting active ingredient in the pharmaceutical field, mainly in the therapy of diseases of the muscle-skeletal system, and as starting materials for the preparation of novel antitumor, immunosuppressive, antipsoriasis and antiinflammatory medicaments.

WO 98/15642 discloses a process for the production of colchicinoid glycosyl-derivatives in high conversion yields (up to 90%), starting from colchicinoid compounds such as colchicine, thiocolchicine and derivatives thereof, with an initial concentration up to 1 g/l. The process is based on a preliminary, regioselective demethylation step of the C-3 methoxy group bound to the aromatic ring of the colchicinoid, and a subsequent glycosylation of the demethyl derivative at the same molecular site.

The process of the present invention, while maintaining the same high conversion yield of the former, allows the transformation of considerably higher amount of total substrate, thus improving both the total productivity, expressed as the total amount of product obtained per liter per batch, and the specific productivity, expressed as the amount of product obtained per liter per time unit (i.e: hour) during the biotransformation process.

The process of the invention is characterised by the activation mechanism of the glycosylating step, based on the induction of the specific enzyme. In fact, it has been surprisingly found that the enzyme involved in the glycosylation step is efficiently induced by demethylated colchicinoids such as 3-O-demethylcolchicine (DMC) or 3-O-demethylthiocolchicine (DMTC). An addition of small amounts (200-600 mg/l) of the 3-demethyl derivative in the early stages of the biotransformation process, or preferably in the preliminary seed culture, is useful for an early activation of the glycosylating system. In such condition, the demethylated intermediate, step-by-step released by the demethylating enzyme, can be efficiently converted into the final glycosyl-derivative, and the biotransformation can proceed very fast, during the first 15-18 hours of fermentation. Moreover there is no significant accumulation of the intermediate, that means no inhibition of the demethylating activity and high conversion rate. The biotransformation is completed after 18-21 hours and is therefore considerably faster than that of the known process (26-28 hours). The conversion yield remains very high, from 80% to 100%, usually about 90-95%, but with a considerable increase of total transformed substrate and, consequently, of final product.

The invention therefore provides a process for the preparation of 3-O-glycosylcolchicinoid compounds of formula (I),

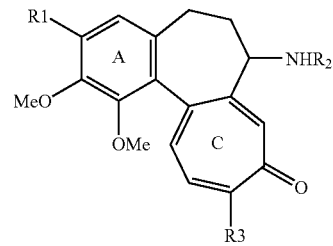

wherein $R_1$ is an O-glycosyde residue, $R_2$ is hydrogen or $C_1$-$C_7$ acyl, $R_3$ is $C_1$-$C_6$ alkoxy or $C_1$-$C_6$ thioalkyl, comprising the biotransformation of compounds in which $R_1$ is OH or methoxy by means of *Bacillus megaterium*, characterised in that demethylated colchicinoids are used to induce the glycosylating enzyme system.

$R_1$ is preferably an O-glucoside residue.

A preferred embodiment of the process of the invention, consists in a multiple, fractionated feeding of the substrate, in combination with a nitrogen and a carbon source, like peptone and glucose. This condition, by assuring a stable growth rate of the microbial culture, allows a relevant increase of the total substrate added to the fermentation batch (2-4 g/l, instead of 1 g/l) and consequently of the productivity of the process (up to 2.5-5.2 g/l of glycosylated product per single batch, instead of 1-1.2 g/l), without any loss of conversion efficiency and risk of toxic effects on the bacterial culture, due to a considerable accumulation of the untransformed substrate.

The present invention is also advantageous in view of the reduced time of the process, resulting in a high viability of the culture and a limited cell lysis, with reduced cell debris formation and considerable advantages for the downstream processing and the recovery of the product. This advantage can be further improved by the use of absorption resins, like XAD 1180 (Rohm & Haas) or HP 21 (Mitsubishi), useful for a selective absorption of the colchicinoid compounds and an efficient product recovery from the fermentation broth.

A further advantage concerns the possibility of a semi-continuous process, by recovering the main fraction (75%-90%) of the final fermentation broth, containing the product, adding new fermentation medium to the remaining part of the broth in the bioreactor, and starting with a new batch. This approach can be extended to repeated fermentation steps, with a proportional increase of the total productivity.

Moreover the constant regioselectivity of the catalysis assures, in addition to the remarkable production yields, a high quality of the resulting product, allowing a purity $\geq$99% with a simple downstream processing and a reduced incidence of the step of purification and recovery of the product. This aspect implies further advantages in terms of solvent limitation and high environmental compatibility of the process.

The *Bacillus megaterium* microorganisms usable in the present invention are the same described in WO 98/15642, herein incorporated for reference.

They can be selected on different agar media containing an organic nitrogen source (peptones, yeast extracts, meat extracts, asparagine, etc.), a carbon source (glycerin, starch, maltose, glucose, etc.), with pH 5 to 8, preferably 6-7. The incubation temperature ranges from 20° to 45° C., preferably 28°-40° C.

The culture media used for the conservation of the culture are typical microbiological substrates, containing organic nitrogen sources (peptones, yeast extracts, tryptone, meat extracts, etc.), a carbon source (glucose, maltose, glycerin, etc.), at pH 5 to 8, preferably 6-7. The incubation temperature ranges from 20° to 45° C., preferably 28°-40° C.

The selected microorganisms can be assayed for the capability of growing in submerged culture, in the presence of colchicinoid compounds, added as described in the present invention, and of transforming the latter into the corresponding 3-glycosyl derivatives.

Said assays were carried out in 100 ml flasks containing 20 ml of liquid medium, with different medium formulations, comprising one or more organic nitrogen sources (yeast extracts, peptones, tryptone, casein hydrolysates, meat extract, corn-step liquor, etc.), one or more carbon sources (glucose, glycerol, starch, saccharose, etc.), inorganic phosphorous and nitrogen sources, and inorganic salts of various ions ($K+$, $Na+$, $Mg++$, $Ca++$, $Fe++$, $Mn++$, etc.).

The culture samples can optionally be subjected to mutagenic treatments, by means of the conventional mutagenesis techniques (irradiation with UV rays, etc.) to induce mutants having a specific bioconversion activity which can be evaluated with the same procedure as above.

The capability of the selected bacteria of transforming into the respective 3-glycosyl derivatives colchicinoid substrates, added to the culture broth in repeated fractions, together with a carbon and a nitrogen source, has been confirmed by means of bioconversion assays in flasks, in a 300 ml scale, containing different medium formulations, comprising one or more organic nitrogen sources (yeast extracts, peptones, tryptone, casein hydrolysates, meat extract, corn-step liquor, etc.), one or more carbon sources (glucose, glycerol, starch, saccharose, etc.), inorganic phosphorous and nitrogen sources, and inorganic salts of various ions ($K+$, $Na+$, $Mg++$, $Ca++$, $Fe++$, $Mn++$, $NH4+$, etc.).

Bacterial growth and biotransformation are supported by one or more organic nitrogen sources, preferably meat extract, peptone, tryptone, casein hydrolysates, corn-steep liquor, etc. Carbon sources useful for growth and biotransformation are glucose, fructose, saccharose, glycerol, malt extract, etc., preferably glucose, fructose and glycerol. The culture medium contains moreover inorganic phosphorous sources and salts of $K+$, $Na+$, $Mg++$, $Mn++$, $NH4+$, etc.

The carbon source useful for in process feeding are preferably glucose and fructose. The nitrogen source for in process feeding is preferably an organic source, like peptone, casein hydrolysate, tryptone, or an inorganic one, like ammonium sulphate, or a combination of both.

Preliminary experiments have shown that the introduction, before the biotransformation step, of a submerged seed culture, containing a medium formulation similar to that of the production medium, results in a very homogeneous and highly active microbial population at the beginning of the biotransformation.

Additional experiments have been performed using different fermentation parameters, like amount, time and modality of substrate addition, feeding ratio, incubation time, inoculum ratio, etc.

An early addition of a demethyl colchicinoid as inducer, at the beginning of the biotransformation step or, better, during the preliminary seed culture, can considerably increase the conversion efficiency and the total productivity of the process.

Further increase can be achieved by feeding the substrate to be converted in more fractions during the process, in combination with a carbon source and a nitrogen source.

A typical procedure, combining the parameters described above, can therefore be based on the following schedule:
- a preliminary addition of a 3-O-demethyl colchicinoid (200-600 mg/l, preferably 300-500 mg/l) in the seed culture;
- addition of aliquots (300-800 mg/l, preferably 500-600 mg/l) of the colchicinoid substrate to be converted, at the beginning and every 1-3 hours, preferably 1.5-2.5 hours, during the first 14-18 hours, preferably 15-16 hours of biotransformation;
- addition, at each time of the substrate feeding, of a solution containing the following raw materials:
  a) peptone, or tryptone, or caseine hydrolysate, at a final concentration between 2 and 4 g/l, preferably 2.5-3.5 g/l (also in combination with ammonium sulphate 1-3 g/l, preferably 1.5-2.5 g/l);
  b) glucose or fructose, at a final concentration between 5 and 15 g/l, preferably 8-12 g/l.

Considering a total fermentation time of 20 hours, an initial substrate concentration of 500 g/l, an in-process feeding interval of 2 hours and a total number of 7 feeding steps (last substrate addition at 14th fermentation hour), a total substrate amount of 4 g/l (instead of 1 g/l, as described in WO 98/15642) will be added to the culture.

The biotransformation can be performed at 25°-35° C., preferably at 28°-32° C., at pH between 4 and 8, preferably 5-7, in stirred flasks on a rotary shaker.

The biotransformation of the invention can be scaled up to fermentation tank level, keeping the culture conditions unchanged, in particular as far as culture medium, temperature and processing times are concerned. In order to obtain good growths, adequate levels of stirring-aeration are important, in particular aeration levels of 1-2 liters of air per liter of culture per minute (vvm), preferably of 1.4-1.8 vvm, are required. In such condition the process is very fast and after 20-21 hours the biotransformation is completed.

The product is extracellular and can be extracted from the culture broth after separation of the biomass from the liquid fraction by centrifugation and recovery of the supernatant, or microfiltration and recovery of the permeate. The culture can be treated with alcohols, in view of an optimum recovery of the product.

The purification can be performed by chromatographic techniques, liquid-liquid extraction with alcohols and lipophylic organic solvents and crystallization, as described in WO 98/154621.

The following examples disclose the invention in further detail.

EXAMPLE 1

An aliquot of frozen culture of *Bacillus megaterium* is utilized for the inoculum of seed cultures (i.e.: preculture) in 1000 ml Erlenmeyer flask, containing 250 ml of medium SF2 (Table), added with 3-O-demethylthiocolchicine to a 0.4 g/l final concentration. Said cultures are incubated overnight at 30° C., on a rotary shaker, at 250 rpm. After incubation, 500 ml of preculture are transferred in sterile into a 14 l fermenter, containing 9.5 l of fresh medium SF2 (see Table 1), added with thiocolchicine to a 0.5 g/l final concentration. The fermentation is carried out at 30° C., keeping suitable levels of stirring-aeration (stirring up to 900 rpm; aeration 1 to 1.8 vvm, depending on the culture growth). Every 2 hours thiocolchicine (0.5 g/l final concentration), peptone (2 g/l), ammonium sulphate (2 g/l) and glucose (10 g/l) are added to the culture, during the first 14 hours of fermentation. Before each addition (i.e.: every 2 hours) samples from the culture broths are taken and subjected to the following analysis:

Growth level, as optical density (OD) at 600 nm;
Sterility and purity analysis of the strain on LB Agar;
Microscope morphology (Gram stain);
Analysis of the thiocolchicoside content, by TLC and HPLC.

TLC analysis is performed on silica gel, with an acetone:ethyl acetate:water 5:4:1 eluent system. For the HPLC analysis, 1 ml fractions of culture broths are added with 9 ml of methanol and centrifuged at 13,000 rpm for 2 minutes. The content in thiocolchicoside of the supernatant is analysed by reverse phase HPLC, with isocratic elution, by means of the water:acetonitrile 80:20 eluent system. The HPLC analysis proves that the conversion of thiocolchicine into thiocolchicoside starts very early and is almost completed after 20 hours. A total amount of 4 g/l of thiocolchicine are transformed into 5.2 g/l of thiocolchicoside, with a 96% conversion yield and a specific productivity of 0.26 g/l·h of glucosylated colchicinoid.

EXAMPLE 2

The final culture broth from the fermentation (total volume: about 10 l), containing about 52 g of thiocolchicoside as determined by HPLC analysis, is subjected to cross-flow microfiltration on a 0.22 μm ceramic cartridge, to separate the cells from the broth. The permeate is absorbed on a column filled with a XAD 1180 (Rohm and Haas) absorption resin. After washing with water, the product is eluted with methanol. The methanol eluate is concentrated to dryness under vacuum, then redissolved in methanol. After extraction with methylene chloride, the alcohol fraction is concentrated to dryness and redissolved in an ethanol-methylene chloride, 1:1 mixture. After clarification with silica gel, the solution is concentrated under vacuum; methylene chloride is then substituted with ethanol. The resulting suspension is concentrated and left to crystallize. A second crystallization with ethanol is carried out after further redissolution steps of the solid in ethanol-chloroform mixtures and clarification on silica gel. A total amount of 49.9 g of product are obtained after purification, with a purification yield of 96% and a purity of 99.5%.

The resulting product, analysed by HPLC, C-NMR, H-NMR and mass spectrum, turns out to be the same as the thiocolchicoside standard.

COMPARATIVE EXAMPLE 3

The procedure described in Example 1 is repeated, but thiocolchicine is totally added in a single fraction, at a final concentration of 4 g/l, at the beginning of fermentation. The resulting growth is very poor and is practically blocked after a few hours of incubation. Evident cell lysis is detected by microscopic analysis. No significant biotransformation is shown by TLC and HPLC analysis.

COMPARATIVE EXAMPLE 4

The procedure described in Example 1 is repeated, but without any addition of 3-O-demethylthiocolchicine in the preliminary seed culture (no enzyme induction). Biotransformation results slower than that as in Example 1, and is stopped after 28 hours, with a final conversion yield of 61%, a total productivity of 3.3 g/l and a specific productivity of 0.118 g/l·h of thiocolchicoside.

COMPARATIVE EXAMPLE 5

Corresponding to WO 98/15462

The procedure described in Example 4 is repeated, but thiocolchicine is totally added in a single fraction, at a final concentration of 1 g/l, at the beginning of fermentation, using fermentation medium ST as described in WO98/15462. Biotransformation results slower than that as in example 1, and is stopped after 28 hours, with a final conversion yield of 90%, a total productivity of 1.22 g/l and a specific productivity of 0.044 g/l·h of thiocolchicoside.

The following table shows a comparison in terms of total productivity, specific productivity and conversion yield of thiocolchicine into thiocolchicoside, between the method of the present invention (A) and that of WO098/15642 (B).

|    | Productivity (total) g/l | Productivity (specific) g/l | Conversion yield % |
|----|--------------------------|------------------------------|--------------------|
| A* | 5.22                     | 0.261                        | 96                 |
| B* | 1.22                     | 0.044                        | 90                 |

*substrate (thiocolchicine) added; 4 g/l (A); 1 g/l (B)

TABLE 1

Formulation of the culture media

| 1) LB-Agar (Sterilization: 121° C. × 20')-pH 7 | |
|---|---|
| Triptone | 10 g/l |
| Yeast extract | 5 g/l |
| NaCl | 10 g/l |
| Agar Agar | 15 g/l |
| 2) Broth SF2 (Sterilization: 121° C. × 20')-pH 7 | |
| Glucose | 40 g/l |
| Peptone | 20 g/l |
| Yeast extract | 5 g/l |
| NaCl | 3 g/l |
| (NH$_4$)$_2$SO$_4$ | 3 g/l |
| K$_2$HPO$_4$ | 8 g/l |
| KH$_2$PO$_4$ | 3 g/l |
| MgSO$_4$•7H$_2$O | 0.5 g/l |

The invention claimed is:
1. A process for preparing a 3-O-glycosylcolchicinoid compound of formula I:

I

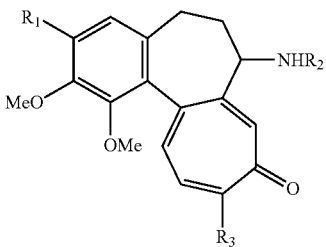

wherein $R_1$ is a O-glycoside residue, $R_2$ is hydrogen or $C_1$-$C_7$ acyl, and $R_3$ is $C_1$-$C_6$ alkoxy or $C_1$-$C_6$ thioalkyl, comprising:

a) contacting *Bacillus megaterium* with a demethylcochicinoid compound selected from the group consisting of 3-O-demethylcholchicine (DMC) and 3-O-demethylthiocholchicine (DMTC), wherein the demethylcochicinoid compound induces a glycosylating enzyme of the *Bacillus megaterium*, to obtain a preliminary seed culture; and b) fermenting a mixture comprising a carbon source, a nitrogen source and a compound of Formula II:

II

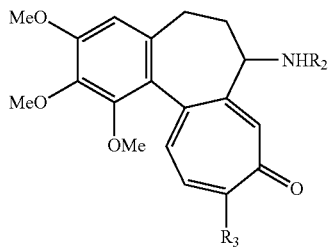

wherein $R_2$ is hydrogen or $C_1$-$C_7$ acyl and $R_3$ is $C_1$-$C_6$ alkoxy or $C_1$-$C_6$ thioalkyl, with the preliminary seed culture to form a broth, wherein multiple fractions of the mixture are added to the broth during the fermentation.

2. The process according to claim 1, wherein the concentration of the demethylated colchicinoid compound is from 200 to 600 mg/l per fraction added.

3. The process according to claim 1, wherein the nitrogen source is peptone and the carbon source is glucose.

4. The process according to claim 1, wherein the final concentration of the compound of formula II added to the fermentation batch is 2-4 g/l.

5. The process according to claim 1, wherein the compound of formula I is recovered by contact with an absorption resin.

6. The process according to claim 1, wherein the process is carried out in a semi-continuous manner comprising recovering a fraction comprising 75-90% of the fermentation broth containing the compound of formula I and adding additional amounts of the mixture to the remaining portion of the fermentation broth.

7. The process according to claim 1, wherein the fractions of the mixture comprising the carbon source, nitrogen source and the compound of formula II are added at the beginning of the fermentation step and every 1-3 hours thereafter during the first 14-18 hours of the fermentation process; wherein each fraction comprises the compound of formula II in a concentration of 300-800 mg/ml; the nitrogen source is ammonium sulfate at a concentration of 1-3 g/l in combination with an additional nitrogen source selected from the group consisting of peptone, tryptone and caseine hydrolysate wherein final concentration of the additional nitrogen source is 2-4 g/l; and the carbon source is selected from the group consisting of glucose and fructose, wherein the carbon source has a final concentration of 5-15 g/l.

8. The process according to claim 1, wherein the fermentation is carried out at 25° to 35° C. and a pH of between 4 and 8.

9. The process according to claim 1, wherein the broth is aerated at a level of 1-2 liters of air per liter of broth per minute.

* * * * *